United States Patent [19]

Matsushita

[11] Patent Number: 5,591,829
[45] Date of Patent: Jan. 7, 1997

[54] ANTIBODIES MODIFIED WITH TOXIC SUBSTANCE

[76] Inventor: Shuzo Matsushita, 22-22, Suizenji 2-chome, Kumamoto-shi, Kumamoto-ken, Japan

[21] Appl. No.: 410,932

[22] Filed: Mar. 27, 1995

Related U.S. Application Data

[63] Continuation of Ser. No. 280,302, Jul. 26, 1994, abandoned, which is a continuation of Ser. No. 999,678, Dec. 30, 1992, abandoned, which is a continuation of Ser. No. 760,807, Sep. 16, 1991, abandoned, which is a continuation of Ser. No. 477,692, Feb. 9, 1990, abandoned, which is a continuation-in-part of Ser. No. 198,957, May 26, 1988, abandoned.

[30] Foreign Application Priority Data

May 29, 1987 [JP] Japan .................. 62-133909

[51] Int. Cl.⁶ ............... C12N 5/12; C07K 16/10
[52] U.S. Cl. ............... 530/388.35; 530/391.1; 530/391.9; 530/391.7; 530/391.3; 435/240.27
[58] Field of Search ............ 530/391.1, 389.4, 530/391.3, 391.9, 391.7, 388.35; 435/240.27

[56] References Cited

U.S. PATENT DOCUMENTS 4,340,535  7/1982  Voison ................. 260/112 B
4,545,985  11/1985  Pastan et al. ............ 424/130.1

FOREIGN PATENT DOCUMENTS 8809181  12/1988  WIPO .

OTHER PUBLICATIONS

Kearney, Fundamental Immunology 1984 pp. 751–766.
Pincus et al. Journal of Immunology. May 1, 1989 vol. 142 3070–3075 No. 9.
Shore et al. Journal of Immunology 1976 vol. 116 No.1 pp. 194–201.
Kozak et al. PNAS. vol. 83 pp. 474–478 Jan. 1986.
Chanh et al. Eur. J. Immunol. 16:1465–1468, 1986.
Ho et al. Journal of Virology, pp. 2024–2028 Jun. 1987 vol. 61 No. 6.
WO87/02775 May 1987 Southwest Foundation for Biomedical Research.
Skinner et al. AIDS Research and Human Retroviruses vol. 4, No. 3 p. 187, 1988.
Fung et al. Biotechnology vol. 5, 1987 p. 940.

*Primary Examiner*—Lila Feisee
*Attorney, Agent, or Firm*—Schweitzer Cornman & Gross

[57] ABSTRACT

The present invention is directed to an antibody or fragment thereof, modified with a toxic substance capable of substantially inhibiting the growth of human cells infected with viruses, which is prepared by conjugating a substance capable of chemically and/or physically inducing cytotoxicity against human cells infected with HIV with an antibody or fragment thereof capable of specifically reacting with at least one antigen of said viruses, by using a pharmacologically inert substance as a carrier. The antibodies according to the present invention may be used, for example, in the diagnosis, prevention and curing of chronic disorders induced by viral infections, e.g. AIDS and leukemia, since they are not only capable of inhibiting the growth of the virus-producing cells and capable of killing such cells but also are capable of neutralizing the viruses without inhibiting the growth of uninfected cells.

3 Claims, 6 Drawing Sheets

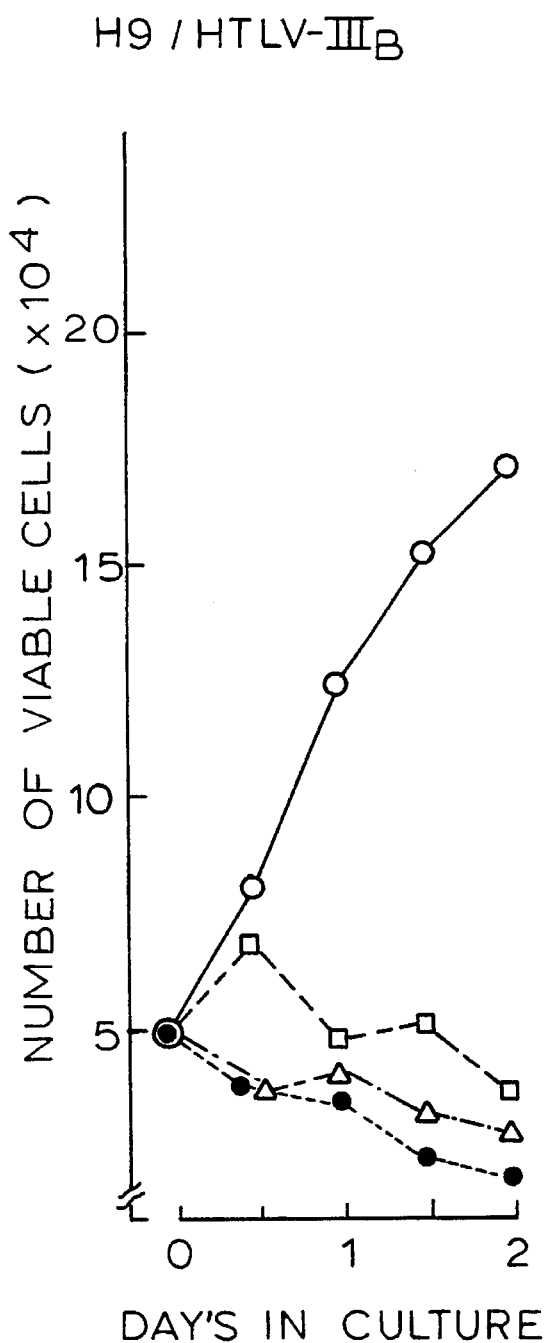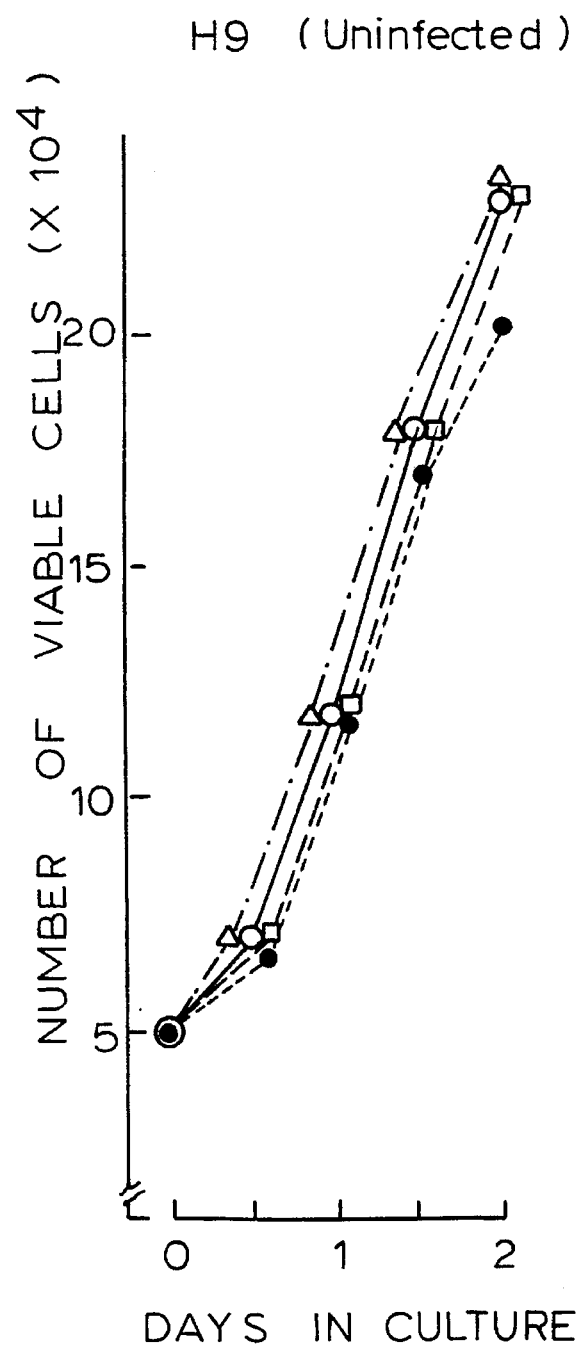

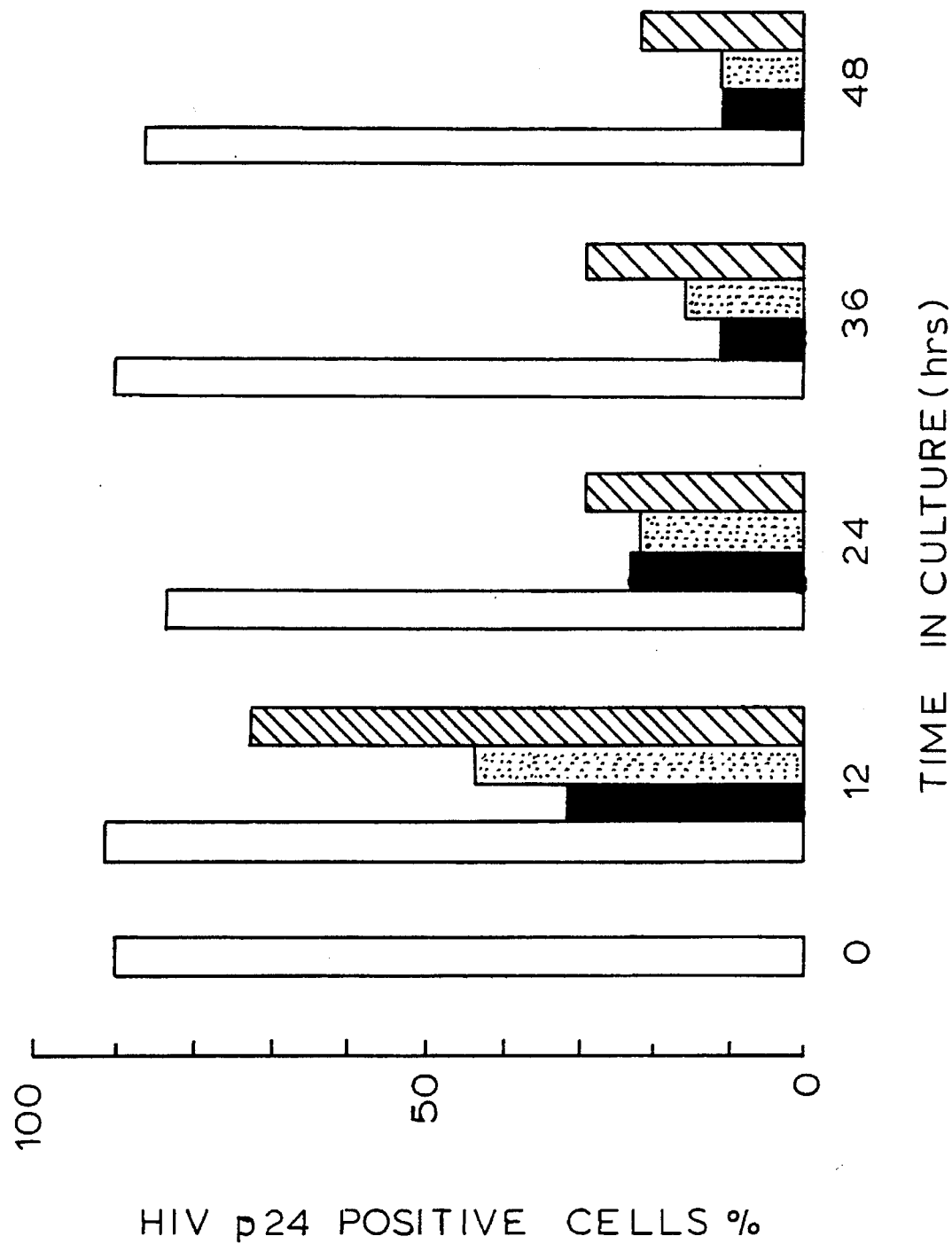

CEM / LAV-1

CEM (Uninfected)

ANTIBODIES MODIFIED WITH TOXIC SUBSTANCE

RELATED APPLICATION

This is a continuing application of U.S. Ser. No. 08/280,302, filed Jul. 26, 1994, now abandoned, which is a continuation of U.S. application Ser. No. 07/999,678, filed on Dec. 30, 1992, now abandoned, which is a continuation of U.S. application Ser. No. 760,807, filed on Sep. 16, 1991, now abandoned, which is a continuation of U.S. application Ser. No. 477,692, filed on Feb. 9, 1990, now abandoned, which is a continuation-in-part of U.S. Ser. No. 198,957 of May 26, 1988, now abandoned.

BACKGROUND OF THE INVENTION

1. Field of the Invention

This invention relates to antibodies modified with a cytotoxic substance, which may be used to treat chronic disorders in humans induced by viral infections, for example, AIDS viruses and leukemia viruses.

2. Description of Prior Art

Nowadays, certain chronic disorders in humans, for example, Acquired Immunodeficiency Syndrome (AIDS), AIDS-Related Complex (ARC) and adult T-cell leukemia, which are induced by the replication of viruses in the body of human hosts, are well recognized as world-wide epidemics.

It is also known that human immunodeficiency virus (HIV), an etiological factor for such disorders is a human retrovirus.

As is well known, prototype HIV are human T-lymphotropic virus type III (HLTV-III) and lymphadenopathy associated virus (LAV), and human T-cell leukemia virus I (HTLV-I) is pathogenic for leukemia and immunodeficiency syndrome.

For example, the most profound hematologic features associated with AIDS are the functional impairment and quantitative depletion of the helper/inducer subset of T-lymphocytes which express the CD4 surface antigen. HIV-induced immunosuppression results in a variety of deficiencies of the host defense system. The immune defect appears to be progressive and irreversible and results in a very high mortality rate.

In the first stage of HIV infection to T cells, cell-free infection viz. attachment of cell-free virons to the target receptor CD4 antigen occurs. However, HIV may also spread by cell-to-cell infection viz. by fusion of infected T cells with uninfected T cells so that the formation of syncytia (polynucleated giant cells) occurs in organs such as the brain and the lymph nodes. The depletion of CD4-positive cells may occur because the HIV-infected T cells are susceptible to the cytopathic effects of HIV.

Another feature of such chronic disorders induced by infection of viruses resides in the fact that the incubation period is very long. It is known that HIV infects not only the helper/inducer subsets of T cells but also the cells of the monocytes/macrophage lineage. It is also known that, in such cases, most of monocytes/macrophages and certain T cells are resistant to the cytopathic effects of HIV and are thus considered to act as the reservoir cells of the viruses.

It is further known that polyclonal antibodies against HIV are present in blood obtained from HIV-infected humans, but the neutralizing activities of such antibodies are, in general, very weak. Thus, even though at the initial stage of the infection, cells infected with the viruses may more or less be killed in the body of the hosts, the immunodeficiency of the hosts gradually falls and eventually the host will die.

The existence of certain structural antigens of HIV including core (gag) antigens and envelope antigens is also known. The viral envelope comprises a 160 kilodalton (gp160) precursor glycoprotein which is subsequently cleaved into 120 kd (gp120) and 41 kd (gp41) glycoproteins present in the viral particles. The external envelope protein of HIV gp120 is the most important glycoprotein with respect to the following characteristics:

(1) Gp120 and/or certain fragments of gp120 are capable of inducing polyclonal neutralizing antibodies in experimental animals. This means that gp120 is at least one of the target molecules of neutralizing antibodies [as disclosed, for example, in Lasky, L. A. et al, Science, 233, 209–212 (1986); Robbey, W. G. et al, Proc. Natl. Acad. Sc. U.S.A., 83, 7023–7027 (1986) and Putney S. D. et al., Science, 234, 1392–1395 (1987).

(2) The infection of HIV is initiated by binding of gp120 to the receptor CD4 molecule. This means that gp120 is a critical molecule for HIV with respect to the infection to target cells [as disclosed, for example, in McDougal J. S. et al, Science, 231, 382–385 (1986)].

(3) The formation of syncytia induced by HIV viz. the cell-to-cell infection of HIV depends on the direct interaction of gp120 with CD4 molecules of the uninfected cells [as disclosed, for example, in Lifson J. D. et al, Nature 323, 725–728 (1986)].

In the case of human T-cell leukemia viruses, it is said that gp46, a glycoprotein antigen on the envelope of HLTV-1 corresponding to gp120 of HIV, represents an important etiological factor.

Various monoclonal antibodies against the protein components of HTLV-III or LAV have hitherto been proposed, as exemplified by those against p24, one of the core antigens present on the inside of the viruses [Veronese F. D., Proc. Natl. Acad. Sci. USA., 82, 5199–5202 (1985): those against the product from the poll gene capable of cording the reverse transcriptase of the viruses [Veronese F. D. et al., Science 231, 1289–1291 (1986); and those against gp41, part of the envelope [Veronese F. D. et al., Science 229, 1402–1405 (1985)]. However, none of the known monoclonal antibodies are capable of reacting with gp120 antigen which is important to treat HIV and to protect against HIV infection and are also capable of neutralizing HIV.

Almost all antiviral agents which have ever been proposed to prevent and/or treat HIV infection appear to act as agents to inhibit HIV-specific enzymes. Thus, for example, azidothymidin and dideoxycytidin are agents to inhibit reverse transcriptase, and castanospermin is an agent to inhibit modification of viral proteins.

Even though these agents are more or less capable of inhibiting the infection of fresh viruses just produced in the body of the patients to uninfected cells, it is difficult to positively kill the cells already infected.

On the other hand, various attempts have been made to specifically kill tumour cells by using antibodies conjugated with a substance which is toxic against the tumour cells (the so-called immunotoxin) [for example, E. S, Vietta et al, Cell, vol. 41, 653–654 (July 1986); and I. Pastan et al, Cell, vol. 47, 641–648 (December 1986)].

It has also been proposed to use monoclonal antibodies conjugated with particles capable of emitting α-rays which are toxic against tumour cells [R. M. Macklis et al, Science vol. 240, 1024–1027 (20 May 1988)]. However, there are still serious problems to be solved in this regard. For example, it is not yet clear whether an antibody Capable of specifically reacting with antigens of tumour cells really exists.

With regard to treatment of chronic disorders induced by viral infections, such an immunotoxin has not yet been proposed by various reasons. Clearly one of the main reasons resides in that any antiviral antibodies which may effectively be used for this purpose has not yet been proposed. Thus, a toxic substance which may advantageously be used for this purpose has not yet been clarified.

The present inventor has proposed a monoclonal antibodies designated as 0.5β antibody having the following characteristics:

(a) capable of substantially neutralizing human immunodeficiency viruses (HIV) by binding to a glycoprotein antigen having a molecular weight of about 120,000, located on the envelope of said viruses;

(b) classified into $IgG_1$;

(c) capable of inhibiting the formation of syncytia between the cells infected with human T-lymphotropic viruses III and uninfected cells by binding to the surfaces of the infected cells;

(d) capable of binding to the precursor of a glycoprotein antigen of HIV, having a molecular weight of about 160,000 dalton; and (e) capable of recognizing an epitope located within a range of Nos. 308–331 of the amino acid sequence of gp120 antigen of human immunodeficiency viruses [measured by the method of Ratner et al. (Nature, 313, 77–284 (1985)].

This monoclonal antibody is disclosed in the parent patent application Ser. No. 198,957 filed in the name of the present inventor.

Although 0.5β antibody is capable of effectively reacting with gp120 of HIV and neutralizing the viruses, it may be difficult to effectively inhibit the growth of the cells infected with the viruses viz. the cells capable of producing the viruses.

The present invention is based upon the discovery that it is possible to obtain an antibody capable of neutralizing the viruses and also capable of inhibiting the growth of the cells infected with the viruses by modifying 0.5β antibody with certain substances.

SUMMARY OF THE INVENTION

The present invention provides antibodies which may be used to effectively treat chronic disorders induced by viral infection such as e.g. AIDS and viral leukemia, and a process for using the same.

According to one feature of the present invention, there is provided a cytotoxic antibody or fragment thereof, which is obtained by conjugating a substance capable of chemically and/or physically inducing cytotoxicity against virus-infected human cells with an antibody or a fragment thereof capable of specifically reacting with at least one antigen of a virus, the conjugation being effected using a pharmacologically inert substance, said cytotoxic antibody or fragment thereof being capable of substantially inhibiting the growth of the human cells infected with said virus.

By using an effective amount of the antibody or fragment thereof according to the present invention, it is possible at least to inhibit the growth of the cells infected with viruses. The viruses are killed owing to the loss of the support for replication because the resultant antibody or fragment thereof is capable of specifically reacting with said at least one antigen.

According to another feature of the present invention, there is provided an antibody or fragment thereof to treat disorders caused by infection of human immunodeficiency virus (HIV), which is prepared by conjugating a substance capable of chemically and/or physically inducing cytotoxicity with a monoclonal antibody using a pharmacologically inert substance as a carrier; said monoclonal antibody being (a) capable of specifically reacting with a glycoprotein having a molecular weight of about 120,000 dalton and located on the envelope of HIV;

(b) classified into $IgG_1$;

(c) capable of inhibiting the formation of syncytia between the cells infected with HTLV-III and uninfected cells;

(d) capable of binding to the precursor of a glycoprotein antigen of HIV, having a molecular weight of about 160,000 dalton:

(e) capable of recognizing an epitope located within the range of Nos. 308–331 of the amino acid sequence of gp120 antigen of HIV; thereby to result in an antibody or fragment thereof capable of substantially inhibiting the growth of the human cells infected with said virus and neutralizing said infected cells.

This antibody or fragment thereof may advantageously be used to treat AIDS and AIDS-related chronic disorders because it is possible to effectively inhibit the growth of the cells infected with HIV and are also to neutralize these cells with good results, while uninfected cells are not inhibited.

DESCRIPTION OF SPECIFIC EMBODIMENTS

The present invention will be described in more detail as follows.

The present relates to HIV such as HTLV-III and LAV.

In this specification, the term "modification" denotes the conjugation of the antibody with a substance capable of inducing cytotoxicity (referred to as toxic substance in this specification) chemically and/or physically by using a pharmacologically inert substance viz. by means of an inert carrier. The term "neutralizing" used herein denotes the inhibition of HIV infection viz. the cell-free and/or cell-to-cell infections such as the formation of syncytia by the fusion of HIV-infected cells with uninfected cells induced by the interaction of gp120 with CD4-positive molecules. The term "treatment" used herein denotes diagnosis, prevention and curing of the disorders caused by viral infections.

The antibodies of the present invention may be used with advantage to treat disorders induced by viral infection because it is possible to at least inhibit the growth of the cells infected with the viruses and finally kill them, whilst not inhibiting the growth of uninfected cells. Moreover, it is possible to effectively neutralize the viruses.

The toxic substances which may be used for the purpose of the present invention may be selected with respect to undesired side effects against humans, for example, antigenicity and toxicity.

Examples of toxic substances suitable for this purpose include those originating from microorganisms and plants e.g. diphteria toxin, exotoxin originating from microorganism, ricin, abrin, pokeweed antiviral protein, saponin and geronin [cf. I. Pastan et al., Cell, vol. 47, 641–648 (1968)]. Also, it is possible to use certain toxic substances proposed for treating tumours and certain anti-tumour agents.

It may also be possible to use α-ray-emitting particles proposed in the field of treatment of tumours. Such a α-ray-emitting particles are exemplified by $^{212}$bismuth [R. M. Macklis et al., Science vol. 240, 1024, May 20, 1988]. Although the antibodies conjugated with the toxic substance according to the present invention may be polyclonal or monoclonal, it is preferred to use monoclonal antibodies, for example, in view of the efficiency of the toxic substance conjugated.

Particularly good results may be obtained with the use of 0.5β monoclonal antibody. This antibody may be obtained by using a hybridoma cell prepared by the present inventor and designated as 54'CB1. 54'CB1 was filed with the European Collection of Animal Cell Culture Portion Down, Salisbury, Wilts, England on 14th May 1987 under the provisions of the Budapest Treaty and assigned with a deposition number of 54'CB1ECACC No. 87051401.

In order to conjugate the antibody with the toxic substance, it is preferred to use, for example, a pharmacologically inert reagent or carrier having active radicals on both sides. Suitable carriers may be selected, depending upon various factors e.g. the type of antibodies and toxic substances.

In one preferred embodiment of the antibody modified with toxic substance of the present invention comprises 0.5β monoclonal antibody conjugated with ricin [Ricin A chain, commercially available from E.Y, Laboratories, U.S.A.] or with exotoxin originating from a microorganism of the genus Pseudomonas, and may be obtained by the use of N-succinimidyl-3-(pyridyldithio)propionate [commercial product of Pharmacia Fine Chemicals AB., Sweden].

It is possible to conjugate, for example, 1–2 molecules of the toxic substance with one 0.5β monoclonal antibody.

The activity of the modified antibody may be measured, for example, in the following manner.

The cells infected with HIV and uninfected cells, for example, H9/HTLV-III$_B$ cells [JA-A-500767/86; ATCC CRL No. 8543] and H9 cells were respectively cultured using a medium containing the toxic substance to measure the degree of propagation and the degree of appearance of the viruses. In the case where the antibody has been appropriately modified with the toxic substance, it has been observed that the growth of the cells is significantly inhibited, depending upon the concentration of the toxic substance, whilst H9 cells are not killed and uninfected cells are not significantly inhibited.

It has also been observed that, in accordance with an increase of the degree of the appearance of the viruses from the infected cells, the infected cells inherently having a lower degree of the appearance of the viruses exhibit a higher survival ratio.

For example, in the case where 0.16 μg/ml of 0.5β monoclonal antibody conjugated with Ricin A chain (hereinafter referred to as RAC-0.5β antibody) was added to RPMI-1640 medium containing 15% fetal calf serum, it has been noted that all H9 cells infected with HTLV-III$_B$ were killed within a period of 10 days, whilst uninfected H9 cells were not significantly inhibited.

Moreover, in some cases where the antibody was applied to the cells at a lower concentration, for example, 1/5 to 1/10 of 0.16μg/ml, the death of nearly all of the infected cells was noted.

From these results as a whole, it has been found that the degree of the inhibition was substantially proportional to the degree of the concentration of the antibody. Thus, it is apparent that significant inhibition may be possible even by using RAC-0.5μ antibody at a very low concentration (for example, by dilution of 0.16μg/ml to 1:several hundreds or 1: several thousands).

Also, similar good results were obtained by the use of 0.5μ monoclonal antibody conjugated with exotoxin of Pseudomonas origin (hereinafter referred to as PE-0.5β antibody).

H9 cells infected with HTLV-III$_B$ were cultured using a medium containing RAC-0.5β antibody of the present invention, and then VAK5 monoclonal antibody [capable of specifically recognizing p24 antigen, a core (gag) antigen of HTLV-III$_B$ and its precursor [disclosed in Gann (Jpn. J. Cancer Res. 78, 235–241, 1987)] was applied to investigate the number of p24 positive cells. It was found that the number of cells capable of producing a large amount of viral protein was decreased in accordance with the progress of the culturing.

The peripheral blood collected from the patients infected with HIV was investigated by the laser flow cytometry. In some cases, it has been found that antigen reactive with 0.5β antibody is present in the fractions containing monocytes/macrophages. In such cases, it was possible to kill the infected cells without deleterious influence upon other cells by the use of the modified antibody of the present invention.

As is apparent from the above-mentioned findings, by using the modified antibodies according to the present invention, it is possible to specifically challenge the cells infected with HIV in the body of the patients with chronic disorders induced by the viral infection. It is also possible to at least inhibit the replication of the viruses effectively or to kill the cells. Moreover, under certain conditions, it is possible to neutralize HIV viruses with good results.

The modified antibodies of the present invention are capable of inhibiting the growth of the cells infected with viruses and also capable of killing such cells. Thus the modified antibodies of the present invention may be used with advantage for the treatment, for example, diagnosis, prevention and curing, of chronic disorders of humans induced by viral infection.

BRIEF DESCRIPTION OF DRAWINGS

In the drawings which illustrate preferred embodiments of the present invention:

FIGS. 1A and 1B show the inhibiting effect of RAC-0.5β antibody of the present invention against H9/HTLV-III$_B$ cells infected with HTLV-III$_B$ and uninfected H9 cells.

FIG. 2 is the pattern obtained by the indirect immunofluorescein antibody method showing the inhibition against infected cells H9/HTLV-III$_B$.

EXAMPLES AND EXPERIMENTS

The following non-limiting examples and experiments illustrate the present invention, where the treating temperature was ambient and the pH of the phosphate buffered saline was adjusted to about 7.0–7.4 (for example, 7.2) unless otherwise specified.

EXAMPLE 1

As a toxic substance, Ricin A chain (commercially available from E.Y. Laboratories Inc., U.S.A.) was used (hereinafter referred to as RAC). As a starting antibody, 0.5β monoclonal antibody disclosed in the Reference Example hereinafter was used. In order to conjugate a toxic substance with the starting antibody, N-succinimidyl-3-(2-pyridyldithio)propionate having two active radicals (commercial product of Pharmacia Fine Chemicals AB., Sweden; hereinafter referred to as SPDP) was used.

Dimethylformamide (5 μl) containing SPDP (30 mM) was added to 1 ml of a purified solution of 0.5β antibody (1 mg/ml). The mixture was well stirred and incubated for 30 minutes. The reaction solution was dialyzed for 60 minutes against a buffered-solution (pH 4.5; 1 l) containing sodium chloride (0.15M) and sodium acetate (0.05M) to obtain SPDP-0.5β antibody viz. SPDP linked with 0.5β antibody.

1 ml of an aqueous solution of RAC (1 mg/ml) which had been purified and treated with dithiothreitol (reducing agent) was cooled to a temperature of 4° C. and dialyzed for one hour against a similar acetate-buffered solution (pH 4.5; 2 l). To the resultant RAC solution (0.7 ml) was added 1 ml of SPDP-0.5β antibody solution. After stirring, the mixture was dialyzed for 18 hours against a phosphate-buffered saline (pH 7.8: 1 l) to obtain RAC-0.5β antibody solution viz. 0.5β antibody conjugated with RAC.

The reaction solution was passed through a column (1×50 cm) packed with Sephacryl 200 (commercial product of Phamacia Fine Chemicals AB, Sweden), gel filtration being effected by using a phosphate-buffered saline to remove unreacted RAC from the product.

1) The eluted active fractions (each about 0.8 ml otherwise specified) were treated in the following manner to assay the concentrations of 0.5β antibody and RAC:

On each occasion, anti-mouse IgG (commercially available from Sigma, U.S.A.; 100 μl) was smeared onto the well of a 96 well ELISA plate [Imuron I, commercially available from Dynatech Inc., U.S.A.). After incubating for 18 hours at a temperature of 4° C., the plate was washed twice with a phosphate-buffered saline. Then, the sample and control were put into different wells and kept for 2 hours. As control, mouse IgG Standard (commercial product of Melloy Inc., U.S.A.) was used.

After washing twice with a phosphate-buffered solution, 100 μl of anti-mouse IgG [Sigma, U.S.A.; diluted with a phosphate-buffered solution (0.1M) containing 1% calf fetal serum to 1:1000 and labelled with alkaline phosphatase] was put into the well to carry out the reaction. After washing the plate 3 times with a phosphate-buffered solution, each material was treated with 100 μl of alkaline phosphatase substrate (Sigma, U.S.A.) to develope colour. In this manner the eluted fractions containing IgG were identified.

2) In a similar manner to that described above with the exception that the reaction was effected by using Rabbit anti-rabbit RAC antibody (commercial product of E.Y. Laboratories Inc., U.S.A.) instead of the secondary antibody, colour was developed using anti-rabbit antibody and alkaline phosphatase substrate (each 100 μl; commercial products of Sigma, U.S.A.) to assay the eluted fractions of RAC in the conjugated product.

3) On each occasion, part of sample (10 μl) was smeared onto the well of the plate, to which was then added each 90 μl of a carbonate-buffered solution (pH 9.6; 0.1M). The plate was incubated for 18 hours at a temperature of 4° C., After washing twice with phosphate-buffered saline, each material in the well was reacted with rabbit anti-RAC antibody (each 100 μl: commercial product of E.Y. Laboratories Inc., U.S.A.).

The reaction solution was treated in a similar manner to that described above to develope colour. In this manner, the eluted fractions containing RAC which was unreacted with 0.5β antibody was obtained.

4) Each sample which was evaluated as being qualified conjugated product from RAC and 0.5β antibody was subjected to high performance liquid chromatography by using Superose 12 column (commercial product of LKB Pharmacia AB, Sweden) and phosphate-buffered saline. As a result, it was found that one molecule of RAC was conjugated with one molecule of 0.5β antibody.

EXAMPLE 2

In a similar manner to that described in Example 1 with the exception that Pseudomonas exotoxin (commercial product of Seikagaku Kogyo K.K., Japan) was used as a toxic substance and that acetate-buffered solution (1 l) was used for dialysis, PE-0.5β antibody, a conjugate of one molecule of PE with one molecule of 0.5β antibody (1.6 ml) was obtained.

EXPERIMENT 1

Inhibiting activities of RAC-0.5β antibody of the present invention against virus-infected cells (H9/HTLV-$III_B$) and uninfected cells (H9) were tested as follows:

After adjustment of the infected cells or uninfected cells, more than 95% of their living cells were able to exercise an exponential-functional propagation.

Then, on each occasion, the cells were cultured at a temperature of 37° C. using a flat bottom culture plate having 96 wells (microtiter plate; commercial product of Falcon Inc., U.S.A.). As culture medium, RPMI-1640 medium (each 0.2 ml; containing 15% fetal calf serum and RAC-0.5β antibody at different concentrations was used, With reference to FIGS. 1A and 1B of the drawings, RAC-0.5β antibody added to respective media were as follows:

4.0 μg/ml (●), 0.8 μg/ml (Δ), 0.16 μg/ml (□), and 0 μg/ml (○).

After culturing for 48 hours, the survived cells were transferred from the well to a 24 well flat bottom culture plate for further culturing using 1 ml each of the same medium.

At the latest, 12 hours after the beginning of culturing using the media containing the antibody at the tested concentrations, the inhibiting effects were observed. The death of the infected cells was noted in all media containing the antibody at the latest 48 hours after the beginning of the culturing, and 10 days after the beginning of the use of antibody-containing media, no living cells were found in all of these media. On the contrary, the propagation of the uninfected cells was insignificantly inhibited even at a concentration of 4.0 μg/ml of the antibody, whilst no inhibition was found in other media containing the antibody.

These findings suggest that the cells having a higher productivity of the viruses viz. the cells having a higher ratio of the appearance of p24 antigen may probably be killed at an earlier stage of culturing in comparison with the cells having a lower productivity of the viruses viz. the cells having a lower ratio of the appearance of p24 antigen, which may probably not be killed to continue the production of the viruses.

In some cases where the concentration of the antibody (0.16 µg/ml) was further diluted, for example, to 1:5~ 1:10, the cells were killed significantly. It has also been found that, as a whole, the degree of the inhibition was proportional to the degree of the concentration of the antibody. Thus, it can be concluded that the antibody of the present invention significantly inhibits the propagation of the cells infected with HIV even at a very low concentration, for example, in the case where the concentration of 0.16 µg/ml is further diluted to a ratio of 1: several hundreds ~1: several thousands.

EXPERIMENT 2

Virus-infected H9/HTLV-III$_B$ cells and uninfected H9 cells were cultured in a similar manner to that described in Experiment 1 for different times.

With reference to FIG. 2 of the drawings, during the culturing, the used media contained RAC-0.5β antibody at the following concentrations:

(A) 4.0 µg/ml, (B) 0.8 µg/ml.

(C) 0.16 µg/ml and (D) 0 µg/ml.

On each occasion, the infected cells were washed twice with phosphate-buffered saline. The cells were transferred to a glass slide for toxoplasma, air-dried and fixed using a solution of methanol/acetone (1:1 v/v). Then each 10 µg/ml of VAK5 antibody which is a monoclonal antibody capable of recognizing p24 antigen of HIV was added to each well of the plate to carry out the reaction with the fixed cells for 30 minutes. After washing the slide with a phosphate-buffered saline, the material was subjected to a reaction for 30 minutes with anti-mouse IgG labelled with fluorescein isocyanate (commercial product of Sigma, U.S.A.; diluted to 1:50). After washing the slide with phosphate-buffered saline, a fluorescein microscope was used to investigate the ratio of the cells positive to p24 antigen. The abovementioned procedure was performed with reference to Gann [Jpn. J. Cancer Res. 78, 238–241 (1987)].

With reference to FIG. 2, it was found that the ratio of the p24-positive cells decreased in accordance with the progress of the culturing time. This finding suggests that the cells are killed at a relatively early stage of culturing in accordance with a higher productivity of HIV antigens. At all concentrations of the tested antibody, all of the infected cells were killed within a test period of 10 days.

EXPERIMENT 3

Figure 3A:
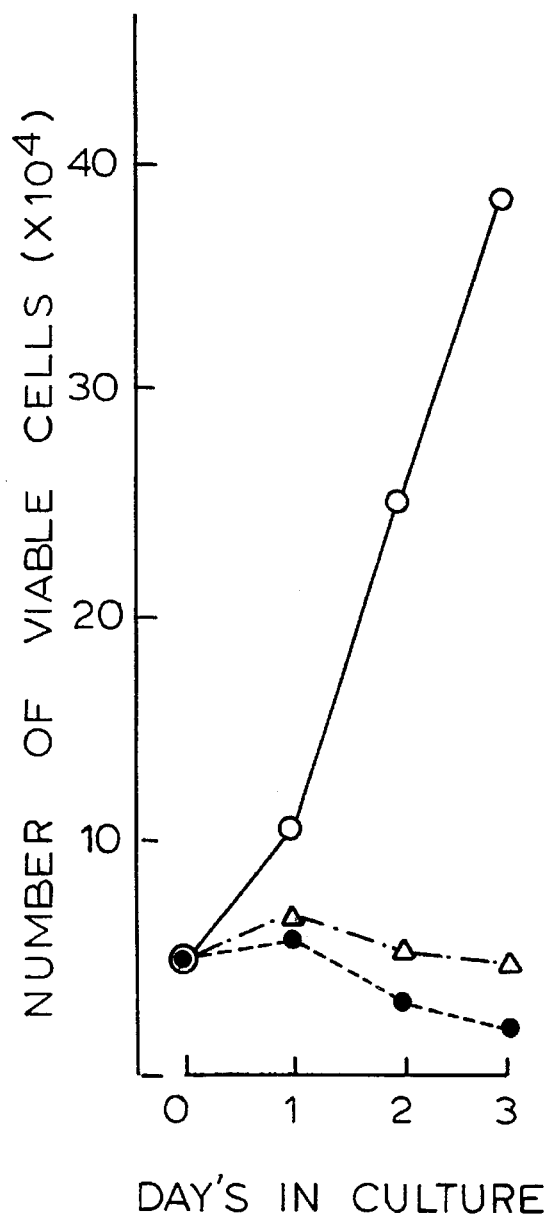
FIGS. 3A and 3B show the inhibiting effect of PE-0.5β antibody of the present invention against CEM cells infected with LAV and uninfected CEM cells.
Figure 3B:
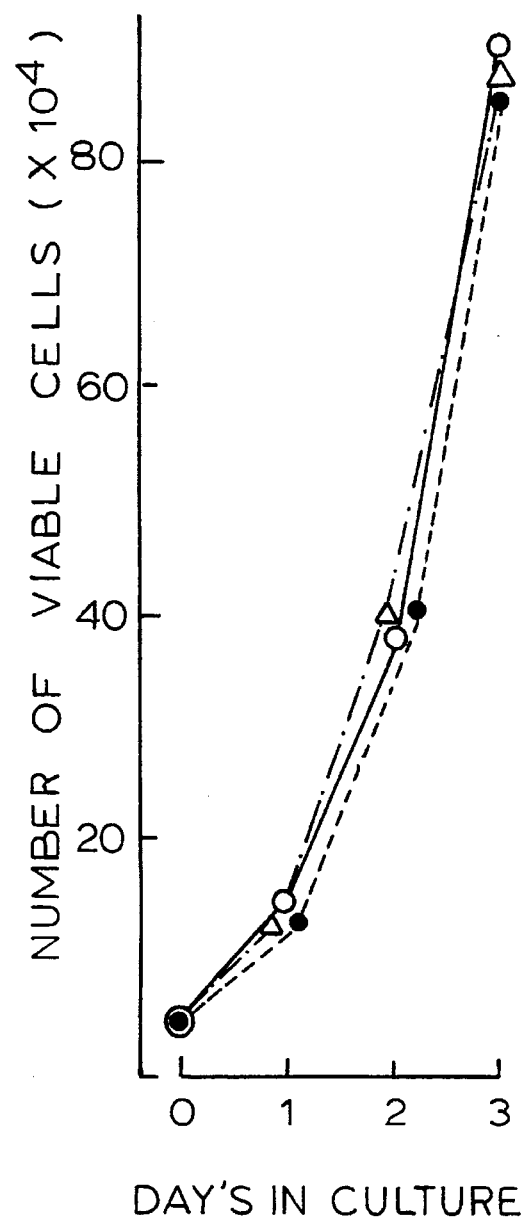

CEM/LAV-1 cells infected with LAV-1 and uninfected CEM cells were cultured in a similar manner to that described in Experiment 1 using a culture plate having 96 wells. The number of the survived cells were counted by the trypan blue method. With reference to FIGS. 3A and 3B of the drawings, during the culturing, the media contained PE-0.5β antibody at the concentrations as follows:

1.0 µg/ml (●), 0.1 µg/ml (△) and 0 µg/ml (○).

On each occasion, after culturing for 46 hours, the culture was transferred to the well of a 24 well culture plate for further culturing for 72 hours. Then the number of cells was counted.

With reference to FIGS. 3A and 3B, it was noted that PE-0.5β antibody of the present invention inhibited the growth of the infected cells strongly and finally killed them, whilst inhibition of the growth of the uninfected cells was not observed.

EXPERIMENT 4

On each occasion, blood (each 20 ml) was collected from the peripheral vein of humans infected with HIV or uninfected humans. Peripheral blood mononuclear cells (PBMC) was separated from the blood by adding 0.2 ml of heparin sodium (1000 unit/ml; Novoheparin, commercial product of Kodama K.K., Japan) and subjected to density-gradient centrifugation in a conventional manner. After washing twice with RPMI-1640 medium, PBMC ($5\times10^6$ cells/ml) was suspended in RPMI-1640 medium containing 200 µg/ml of human IgG [prepared by purifying human serum of the serotype AB with Protein A Sepharose (commercial product of Pharmacia Fine Chemicals AB., Sweden)] and 10% fetal calf serum. The cell suspension was incubated at a temperature of 4° C. for 60 minutes to block Fc receptors located on the surfaces of the cells. The suspension (200 µl) was centrifuged (1000 r.p.m) to collect the cells.

The collected cells were divided into two fractions. To the first sample was added 20 µg/ml of 0.5β antibody, and to the second sample was added 20 µl of MOCP21 antibody [200 µg/ml; anti-mouse antibody; commercially available from Litton Bionetics Bethesda Inc., U.S.A.].

Each sample was well stirred, incubated for 60 minutes and washed twice with phosphate-buffered saline (pH 7.2) containing 2% bovine serum albumin and 0.1% sodium azide (hereinafter referred to as PBS-BSA-Az). Then 100 µl of a fragment of antimouse IgG labelled with fluorescein isocyanate (FITC). [F(ab)'$_2$; commercial product of Sigma, U.S.A.] (diluted with PBS-BSA-Az to 1:40) was added thereto, followed by incubation at a temperature of 4° C. for 60 minutes. After washing well with PBS-BSA-Az, each sample was analyzed using the fluorescein antibody method using Lasor Flow Cytometry Spectrum III (commercial product of Ortho Inc., U.S.A.).

Figure 4B:
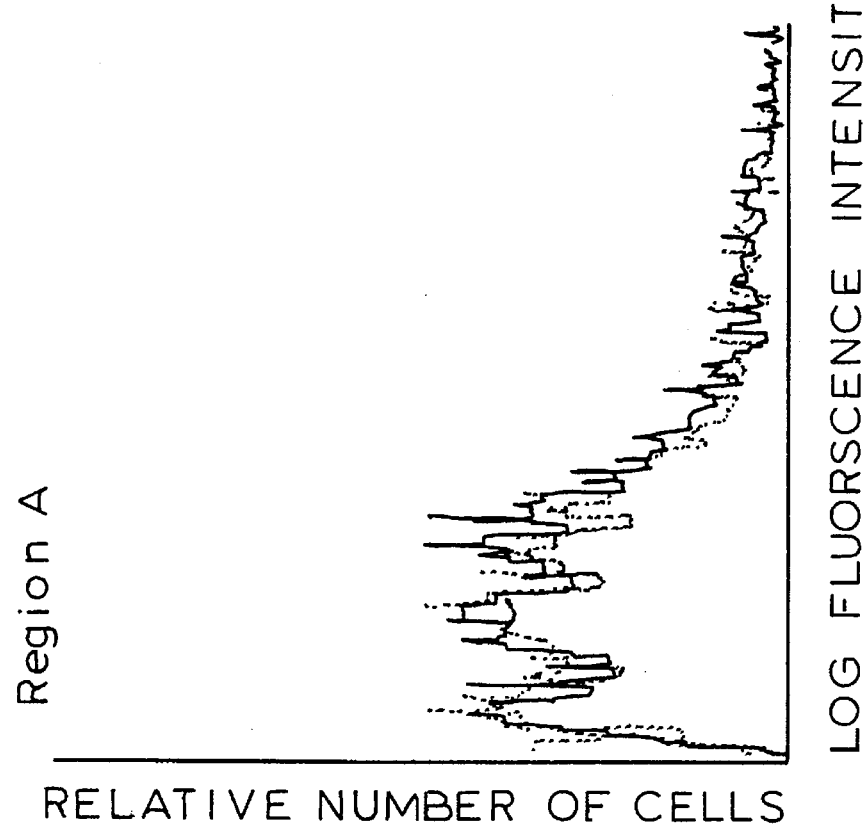
FIGS. 4A and 4B show the reaction of the antibody of the present invention with peripheral blood monocytes of a patient with hemophillia who was infected with HIV.
Figure 4A:
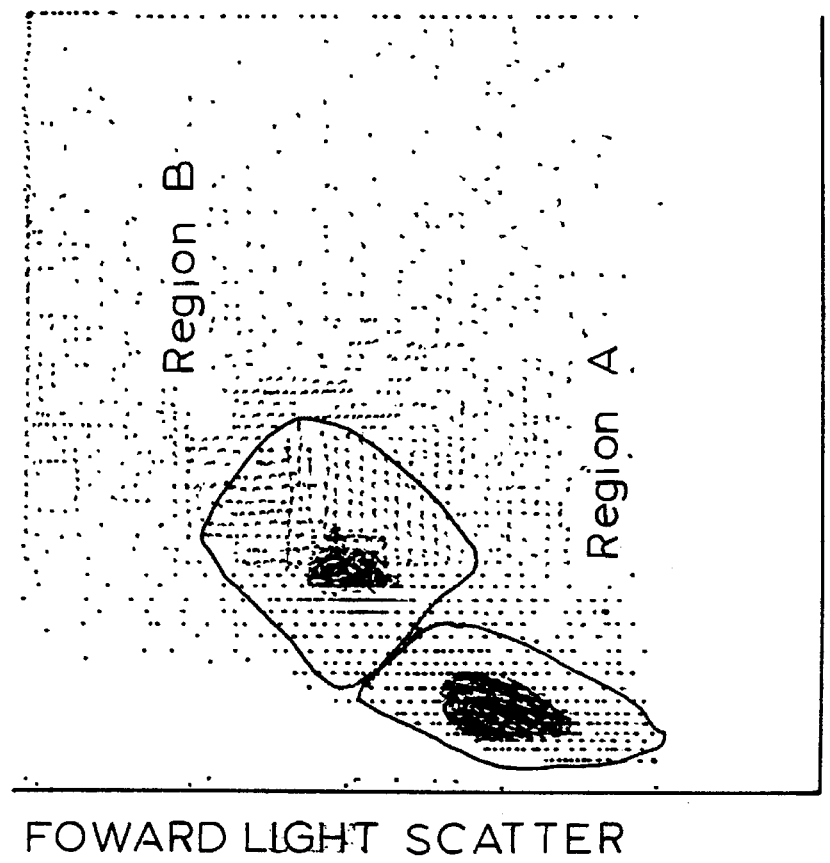
Figure 4C:
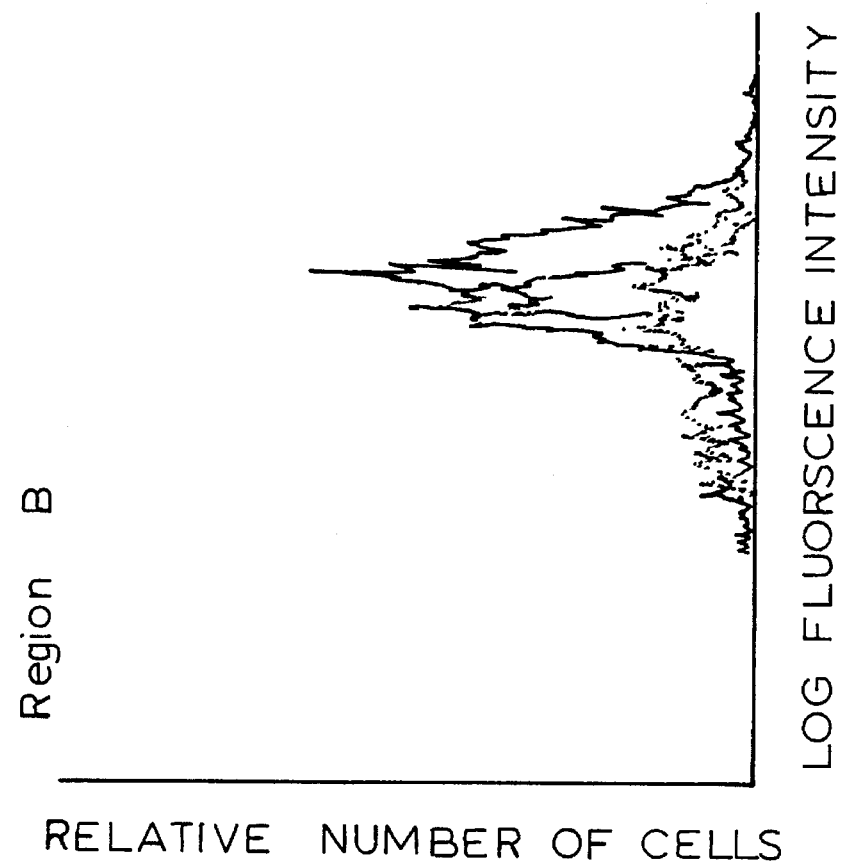

As is apparent from the results shown in Table 1, the presence of the cells which were reactive with 0.5β antibody in the fraction composed mainly of a large number of monocytes/macrophages, was noted in two members among 7 humans infected with HIV, FIGS. 4A–4C of the drawings shows the results obtained by analysis using Lasor Flow Cytometry. which clearly indicates that the cells which were solely reactive with 0.5β antibody were present in Region B containing mainly monocytes/macrophages, whilst such cells were not found in Region B containing mainly lymphocytes. The fractions in Regions B and A were stained respectively by using 0.5β antibody and MOCP21 antibody to determine that antibody reactive with 0.5β antibody was present in Region B.

With regard to the remaining 5 hosts of HIV and two normal humans, it was found that cells reactive with 0.5β antibody were not present in the fractions containing lymphocytes or monocytes/macrophages

TABLE 1

| Host No. | Syndrome | T4/T8 ratio | Positive cells Region A | B |
|---|---|---|---|---|
| 1 | ARC | 0.7 | 1.5 | 18.1 |
| 2 | AC | 1.0 | * | 12.8 |
| 3 | AC | 0.76 | <1 | 2.8 |
| 4 | AC | 1.09 | <1 | <1 |
| 5 | ARC | 0.6 | * | <1 |
| 6 | ARC | 0.5 | <1 | <1 |
| 7 | AC | 0.7 | <1 | <1 |
| Normal PBMC | | | <1 | <1 |

TABLE 1-continued

| Host No. | Syndrome | T4/T8 ratio | Positive cells Region A | B |
|---|---|---|---|---|
| (n = 2) | | | | |
| H9/III$_B$ | | | 60 | * |
| H9 | | | <1 | * |

Notes:
ARC . . . AIDS-Related Complex
AC . . . Silent host of the viruses (asymptomatic carrier)
T4/T8 ratio . . . Ratio of the cells positive to CD4 to the cells positive to CD8 in the peripheral blood
PBMC . . . Peripheral blood mononuclear cells
* . . . Undetectable.

EXPERIMENT 5

In order to clarify whether or not peripheral blood mononuclear cells (PBMC) reactive with 0.5β antibody are killed by RAC-0.5β antibody, PBMC (1×10$^6$ cells) were collected from Host No. 1 shown in Table 1 and cultured at a temperature of 37° C. using a 24 well culture plate and an incubator containing 5% carbon dioxide. Culturing was effected for 40 hours by using RPMI-1640 media containing 15% fetal cattle serum (each 0.1 ml), On each occasion, one of the following materials was added to the medium before the beginning of culturing:

① normal human IgG (200 μg/ml) and MOCP21 antibody (10 μg/ml) [see Experiment 4],
② same as ①,
③ normal human IgG (200 μg/ml) and 0.5β antibody (10 μg/ml),
④ normal human IgG (200 μg/ml) and RAC-0.5β antibody (1 μg/ml; as concentration of 0.5β antibody).

After culturing was completed, each culture was centrifuged to prepare a cell pellet. The pellet was then subjected to reaction with one of the corresponding antibodies as follows:
Samples *
① MOCP21 antibody (20 μg/ml)
② 0.5β antibody (20 μg/ml)
③ 0.5β antibody (20 μg/ml)
④ 0.5β antibody (20 μg/ml)
*before use, diluted to 200 μg/ml with BSA-PBS-Az].

Each reaction product obtained by the reaction for 60 minutes was washed twice with BSA-PBS-Az and treated in a similar manner to that described in Experiment 4. Lasor Flow Cytometry Facstar (commercial product of Becton Dickinson, U.S.A.) was used to analyze the fluorescence-labelled cells to obtain the results shown in FIGS. 5A–5C of the drawings.

Figure 5C:
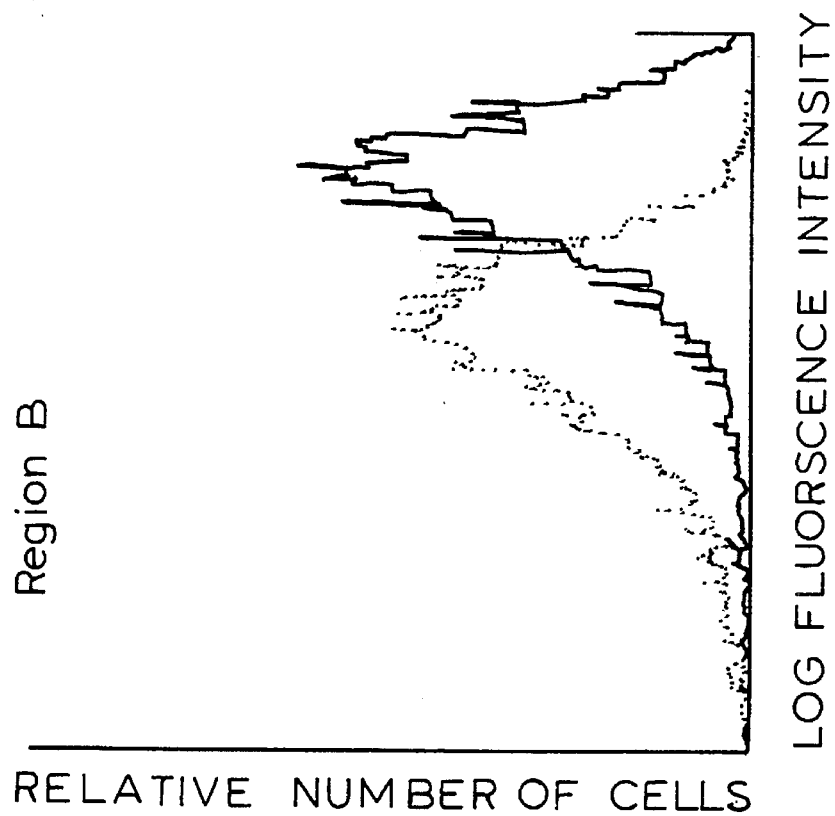
FIGS. 5A and 5B show the inhibiting effect of RAC-0.5β antibody of the present invention against HIV-producing cells collected from peripheral blood of human hosts of HIV.
Figure 5B:
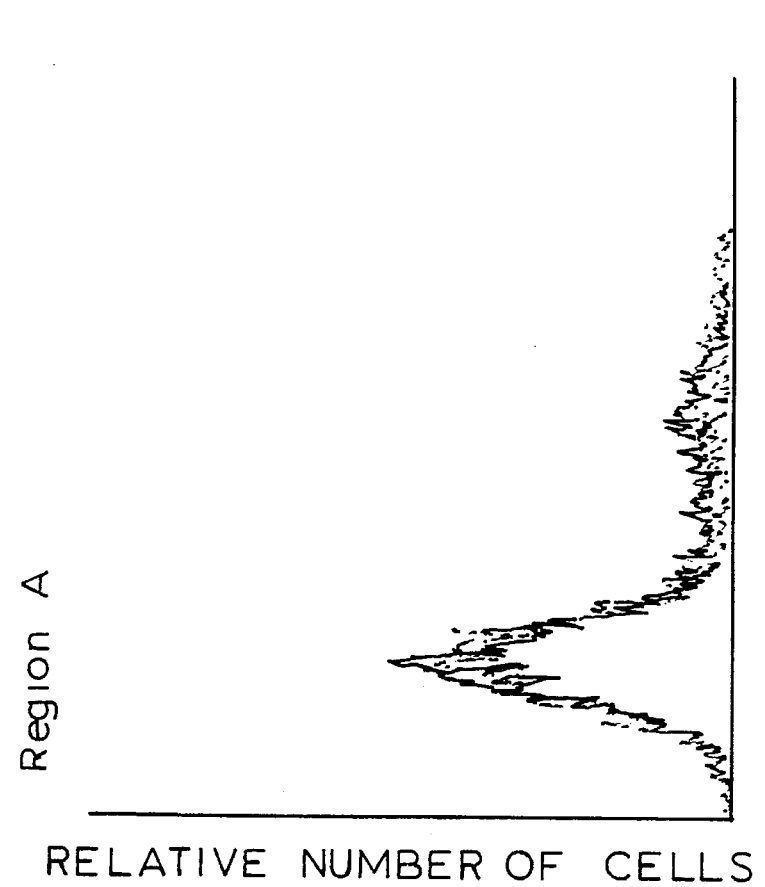
Figure 5A:
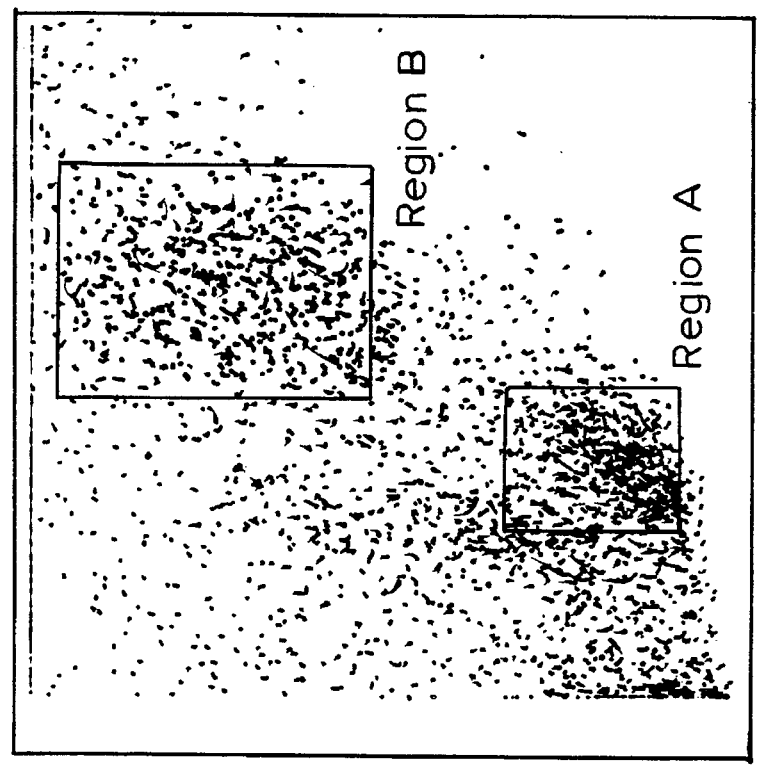

With reference to Region B in FIGS. 5A and 5C, showing the fractions containing mainly monocytes/macrophages, line ② which indicates the case where 0.5β antibody was added to material ② before culturing exhibited significantly strong fluorescein in comparison with line ① which indicates the case where RAC-0.5β antibody was added to material ① viz. the same material as material ② under the same conditions. This finding suggests the existence of the cells positive to 0.5β antibody.

Line ④ which indicates the case where the 0.5β antibody-positive cells were cultured in the presence of RAC-0.5β antibody suggests that a significantly large amount of the positive cells were killed.

With regard to Region A in FIGS. 5A and 5B, showing the fractions containing mainly lymphocytes, it was noted that 0.5β antibody exerted no significant effect.

In both Regions A and B in FIGS. 5A–5C, line ③ indicates the case where material ③ was treated with 0.5β antibody, which is substantially overlapping with line ②. Line ③ is hardly distingushable from line ② which indicates the case where material ② was treated with 0.5β antibody.

From Experiment 5, it is noted that the antibodies of the present invention are effective upon the samples collected directly from human blood.

From the results obtained by the above-mentioned experiments, it is apparent that the antibodies of the present invention are capable of inhibiting the growth of the virus-producing cells and also capable of killing such cells.

The antibodies according to the present invention may be used, for example. for the diagnosis, prevention and curing of chronic disorders induced by viral infections since they are capable of inhibiting the growth of the virus-producing cells and are also capable of killing such cells.

REFERENCE EXAMPLES

1) Preparation of Antigen:

H9/HTLV-III$_B$ viz. H9 cells infected with HTLV-III$_B$ [Science, 224, 497–500 (1984)] were cultured using RPMI 1640 medium containing 10% FCS in an incubator containing 5% CO$_2$ at a temperature of 37° C. for 24 hours.

In a similar manner to that described in the above-mentioned article, the supernatant of the medium was used to purify the viruses. The purified viruses were inactivated by heating for one hour at a temperature of 56° C. and were used as an antigen for the primary immunization.

An antigen prepared in the following manner was used as a booster dose for intensifying the immunization:

The H9/HTLV-III$_B$ cells cultured by the above-mentioned method were washed three times with PBS and were then centrifuged (2000 r.p.m./5 min) to obtain cell pellets. The cells (2×10$^8$) were washed three times with PBS (0.15M; pH 7.2). The cells were solubilized by adding a cell-lyzing buffer solution [prepared by omitting sodium deoxycholic acid from RIPA buffer solution (5 ml) containing 1% Triton-X, 0.5% sodium salt of deoxychloric acid, 0.1% SDS, 0.15M NaCl and 0.05M tris-HCl and having a pH of 7.2] and incubated at a temperature of 4° C. for 60 minutes. The lysate was centrifuged (3000 r.p.m/10 min). The supernatant was collected and heated at a temperature of 56° C. for one hour. The resultant solution was added to FCS-Sepharose [prepared by binding fetal calf serum (20 mg/ml) to Sepharose 4B (1 ml)] and reacted at a temperature of 4° C. overnight (for about 12 hours). The reaction solution was centrifuged (8000 r.p.m./10 min.) to obtain a supernatant which was then used as the test sample.

The sample solution (1 ml) was added to Con-A Sepharose (0.5 ml; commercial product of Sigma, U.S.A.) and was incubated at a temperature of 4° C. overnight (for about 18 hours). The material was placed in a column, and after wishing with PBS, elution was effected using α-methyl-D-glucoside (0.5M; 3 ml). The eluate was collected and divided into small fractions (each 0.5 ml).

Sera were collected from hemophilliac patients who were the healthy carriers of HIV. From the collected sera, one exhibiting the highest antibody titer against the envelope was selected by the Western blotting method and purified to obtain IgG fraction. Each lysate was added to Sepharose 4B bound with the purified IgG (5 mg/l) [hereinafter referred to as anti-HIV-Sepharose] and was incubated at a temperature of 4° C. for more than 4 hours. The anti-HIV-Sepharose was placed in a column, washed with PBS and eluted with 0.2M glycine-buffered solution (pH 2.7). The eluate containing 0.1 mg/ml of the antigen was used as a booster to intensify the immunization.

2) Preparation of Hybrodoma

Purified viruses were inactivated by heating at a temperature of 56° C. for one hour. The viruses (0.1 ml) were mixed with Freund's complete adjuvant (0.1 ml) and used for primary immunization of a Balb/c mouse (purchased from Kuroda Dobutu K.K., Japan). Then a purified antigen solution of virus glycoprotein (each 0.1 ml) mixed with Freund's incomplete adjuvant (each 0.1 ml) was used as a booster dose and was intraperitioneally administered to the animal 3 times at intervals of 2 weeks. Three days after the final immunization, the spleen cells were collected from the mouse in a conventional manner. The spleen cells were mixed with P3-X63-Ag8 (X63) [Nature, 256, 495–497 (1975)], the ratio of the number of the spleen cells to the number of the myeloma cells being 1:5. The mixture was centrifuged (1200 r.p.m./5 min.), followed by removal of the supernatant. The pelleted cells were well loosened and a mixed solution (0.2– 1 ml/$10^3$) of antibody-producing cells) of polyethyleneglycol (PEG 4000; 2 g), MEM (2 ml) and dimethyl sulfoxide (0.7 ml) was added to the antibody-producing cells with stirring. After this, MEM (1–2 ml at a time) was added to the mixture at intervals of 1–2 minutes, followed by addition of MEM to make up a total of 50 ml.

The cell suspension was centrifuged to remove the supernatant. The cell pellets were loosened, and a normal medium (100 ml; prepared by adding 10% FCS to RPMI-1640) was added thereto. The cells were loosened by gentle pipetting.

The cell suspension was poured into each well of a 24-well culture plate in an amount of 1 ml per well, followed by incubating at a temperature of 37° C. for 24 hours using a $CO_2$ incubator. After adding to the culture plate a HAT medium (prepared by adding to the culture plate a normal medium $10^{-4}$M), thymidine ($1.5\times10^{-5}$M) and aminoputerine ($4\times10^{-4}$ M), the culturing was further effected for 24 hours. For 2 days after this, the supenatant (1 ml) was removed and the same amount of fresh HAT medium was added to each well at intervals of 24 hours. The culturing was further effected for 10–14 days at a temperature of 37° C. using a $CO_2$ incubator.

When the presence of the fused cells (about 300) grown in the form of colonies in certain wells was found, on each occasion, supernatant (1 ml) was removed from the well and replaced by fresh HT medium (1 ml; prepared by omission of aminoputerine from HAT medium). Such a replacement by HT medium was further effected for 2 days at intervals of 24 hours.

After culturing for 3–4 days using HT medium, part of the supernatant was collected from each of the above-mentioned cultures to assay the ability to bind to the surfaces of H9 cells infected with HTLV-III$_B$ by the immunofluorescein antibody method. A clone exhibiting the highest binding ability was designated as 54'CB1 which grew vigorously to exhibit the highest productivity of the antibody.

3) Preparation of Monoclonal Antibodies by the use of 54'CB1

Hybridoma cells of 54'CB1 prepared by the method (2) were abdominally given to Balb/c mice [pristane-treated; 8 weeks old] in an amount of $4\times10^6$ cells/mouse. 10–21 days after this, ascites tumour was induced by the hybridoma cells. From the host mice of the ascites tumour, ascitic fluid was collected in an amount of 5–10 ml/mouse. After removal of solids from the ascites by centrifugation (3000 r.p.m/5 min), the salting-out of the supernatant was effected using ammonium sulfate (40%). The solution was dialyzed against 0.04M phosphate-buffered solution containing NaCl (0.03M) and having a pH of 8.0. The residue was passed through a column packed with DE52 (bed volume 50 ml; commercial product of Whatman, U.S.A.) at a flow rate of 20–30 ml per hour to collect IgG fractions which were used as a purified monoclonal antibody (designated as 0.5β antibody).

The monoclonal antibody according to the present invention may be used, for example, for diagnosis, prevention and curing of chronic disorders caused by viral infections since it is capable of inhibiting the growth of virus-producing cells and kill them.

I claim:

1. A cytotoxic antibody conjugate comprising a substance which induces cytotoxicity against HIV-1 infected human cells, said substance being selected from the group consisting of diphtheria toxin, Pseudomonas exotoxin, ricin, abrin, pokeweed anti-viral protein, saponin and gelonin, conjugated with monoclonal antibody 0.5 or a fragment thereof which specifically binds at least one antigen of HIV-1 virus, the conjugation being effected by using a pharmacologically inert bifunctional ligand.

2. The cytotoxic antibody according to claim 1, wherein said monoclonal antibody is prepared from a hybridoma cell line.

3. The cytotoxic antibody according to claim 2, wherein the hybridoma is Hybridoma 54/CB1, ECACC No. 87051401.

* * * * *